United States Patent [19]

Tazuma et al.

[11] 4,060,567
[45] Nov. 29, 1977

[54] METHOD OF REDUCING α-ACETYLENE CONTENT OF HYDROCARBON

[75] Inventors: James J. Tazuma, Stow; Angelo Bergomi, Akron, both of Ohio

[73] Assignee: The Goodyear Tire & Rubber Company, Akron, Ohio

[21] Appl. No.: 722,189

[22] Filed: Sept. 10, 1976

[51] Int. Cl.$^2$ .............................................. C07C 7/00
[52] U.S. Cl. ........................... 260/681.5 C; 208/284; 260/665 R; 260/679 R
[58] Field of Search ...................................... 260/681.5

[56] References Cited

U.S. PATENT DOCUMENTS 2,373,715  4/1945  Soday ................................. 260/681.5
2,398,973  4/1946  Soday ................................. 260/681.5

Primary Examiner—Veronica O'Keefe
Attorney, Agent, or Firm—F. W. Brunner; J. D. Wolfe

[57] ABSTRACT

Hydrocarbon fraction containing diolefins and α-acetylenes are treated with an alkali amide to reduce the α-acetylene content.

7 Claims, No Drawings

METHOD OF REDUCING α-ACETYLENE CONTENT OF HYDROCARBON

This invention relates to a method of removing α-acetylenes from diolefins containing from 4 to 8 carbon atoms and mixtures of said diolefins with monoolefins and hydrocarbons.

The presence of α-acetylenes such as vinyl acetylene, 1-pentyne and 1-penten-4-yne in diolefins and mixtures of diolefins with monoolefins and hydrocarbons (hereinafter called polymerization stocks) has been known to act as a poison for the catalyst, viz. transition catalyst, used to make polymers and stereospecific rubbers of polybutadiene or polyisoprene, for example, the high cis- or trans-type polymers, as well as other diolefin rubbers. Consequently, these polymerization stocks have been treated to remove or neutralize the α-acetylenes present prior to the polymerization step, or larger amounts of catalyst had to be used due to its being poisoned by the impurities.

We have discovered that alkali amides remove α-acetylenes, for example, vinylacetylene, 1-pentyne and 1-penten-4-yne from polymerization stocks. This method is particulary suited when the α-acetylenes are present in small amounts, more specifically at the part per million level. The alkali amide is preferably supported on a suitable support to enhance the reactivity of the amide with the α-acetylenes and to prevent plugging of the reactor during the operation. In fact, unsupported alkali amide is somewhat effective but, beside showing lower reactivity, it use may lead to the plugging of the reactor, since some swelling of the bed occurred during the reaction of the α-acetylenes with the amide.

We have further discovered that the time of contact of the alkali amides with the polymerization stock can be controlled to regulate the level of α-acetylenes in the stock so the α-acetylene level will not interfere with the polymerization catalyst. Thus, by controlling the liquid hourly space velocity (LHSV) between 1 to 50 and preferably 5 to 20, the α-acetylene content of the polymerization stocks can be effectively controlled to acceptable levels. Usually the temperature is controlled between 20 to 250° C. with the preferred range being 20° to 150° C. Pressures above or below atmospheric can be used. Also, the process can be practiced by running continuously or batchwise without the need for solvents or other reactants at high velocities and under mild temperature and pressure conditions, viz. either with fixed bed or fluidized bed operation.

The polymerization stocks of primary usefulness in this invention are the so-called $C_4$, $C_5$, $C_6$, $C_7$, and $C_8$ streams or distillation cuts available as a byproduct of crude oil refining or cracking operations. The so-called $C_4$, $C_5$, etc. cuts or streams generally designate a distillation fraction composed of hydrocarbons containing the number of carbon atoms designated by the subscript. Side streams relatively rich in olefins or diolefins are available as products of the refining and cracking operations and the amount of diolefins can be increased by suitable cracking of the appropriate cut of the desired boiling range and/or fractionation of the streams. Then these cracked or distillate cuts rich in diolefins such as isoprene, butadiene, 1,3-pentadiene, sometimes called the $C_4$ and $C_5$ cuts can be used for polymerization stocks after removal of the impurities or catalyst poisons.

Alkali amides suitable for removal of the α-acetylenes are preferably made by dispersing the alkali metals i.e. sodium, potassium, lithium, rubidium, cesium and/or mixtures thereof over a suitable support and then reacting the alkali metal with ammonia to form the amide.

The pure alkali metals are dispersed over a variety of supports. The alkali metals can be sodium, potassium, lithium, rubidium, cesium, or mixtures thereof. The concentration of the alkali metal on the support can range from 5 to 50 percent, the preferred range being 10 to 40 percent by weight. Alumina is an excellent support but other inert supports are also suitable. These supports include silicates and carbonates or the alkali metals (Group IA of the Periodic System), oxides, silicates and carbonates of the alkaline earth metals (Group IIA of the Periodic System), oxides of metals of Groups IIB, IVB, VIB of the Periodic System, as well as oxides of metals which are known as supports or carriers for catalyst. The alkali metal, after being dispersed on the support, is then treated with ammonia to give the corresponding alkali metal amide.

The nature of this invention and its advantages can be more readily seen from the following illustrative and representative examples wherein all parts and percentages are by weight unless otherwise indicated.

EXAMPLE I

The alumina (Harshaw Chemical Company's AL0401P) was a microspheroidal high activity powder containing 97 percent $Al_2O_3$ having a particle size suitable for fluid bed operation. It has a surface area of 180–200 square meters per gram ($m^2/g$), and an apparent bulk density of 0.85 grams per cubic centimeter (g/cc).

The alumina was dried at 400° C. under vacuum for 1 hour. The desired amount of sodium metal was added at 250° C. in an inert atmosphere. The mixture was kept at 250° C. for 1 hour with occasional stirring, cooled to room temperature and transferred into the reactor where it was treated with gaseous ammonia for 2 hours at 150° C. and atmospheric pressure to obtain a sodium amide on an aluminum oxide support.

Removal of α-Acetylenes from Isoprene Sample

The reactor consisted of a stainless steel tube, 30 centimeters (cm) long and 9.5 millimeters internal diameter (mm.I.D.), packed with a layer of stainless steel packing, a layer of Sodamide/alumina (5 cubic centimeters) and another layer of steel packing. The temperature was monitored by a thermocouple placed internally in the tube in correspondence to the center of the catalyst bed. The crude isoprene was fed into the reactor at the desired flow rate. The purified product was collected in a cold trap and analyzed by gas chromatography. An analysis of isoprene before and after treatment with sodamide is reported below:

Table I

|  | Before Treatment | After Treatment |
| --- | --- | --- |
| Isoprene | 91.0% | 91.0% |
| $C_5$ olefins | 9.0% | 9.0% |
| 1-Pentyne | 16 ppm | — |
| 1-Penten-4-yne | 223 ppm | — |
| Cyclopentadiene | — | — |
| 1-Pentene-3-yne | — | 16* ppm |
| Heavies | — | — |

*From the isomerization of 1-penten-4-yne.

EXAMPLE II

The reactor consisted of a stainless steel tube, 30 cm. long and 9.5 mm. I.D., packed with a layer of stainless steel packing, a layer of sodamide/alumina (5 c.c.) and another layer of steel packing. The temperature was monitored by a thermocouple placed internally in correspondence to the center of the sodamide bed. The butadiene, contained in a cylinder, was metered through a rotometer and passed over the sodamide bed at 25° C. and LHSV of 10. The purified monomer was collected in a bomb cooled at −80° C. At the end of the run a sample of butadiene was withdrawn from the container and submitted to a gas chromatographic analysis. The results are reported in Table II:

Table II

|  | Before Treatment | After Treatment |
|---|---|---|
| Butadiene | 98.6% | 100.0% |
| Vinyl acetylene | 380 ppm. | 36 ppm. |
| Vinylcyclohexene | 1.4% | Not detected |

The purified isoprene stream of Example I and the purified butadiene stream of Example II, free or separated from the contacting agent, were washed with water to remove any trace of ammonia evolved from the reaction between the sodamide and the α-acetylenes, and dried over molecular sieves. The streams were then polymerized with aluminum alkyl-titanium halide catalyst to give the respective high in content polymer without experiencing severe catalyst poisoning.

While certain representative embodiments and details have been shown for the purpose of illustrating the invention, it will be apparent to those skilled in this art that various changes and modifications may be made therein without departing from the spirit or scope of the invention.

What is claimed is:

1. A method of reducing the α-acetylene content of a hydrocarbon fraction which comprises a diolefin containing 4 to 8 carbon atoms and small amounts of α-acetylenes by contacting said hydrocarbon fraction with alkali metal amide dispersed on a support to reduce the α-acetylene content, separating the fraction from support and treating the fraction separated from the support to remove ammonia generated as fraction contacts the alkali metal amide.

2. The method of claim 1 wherein the alkali metal amide rests on an alumina support.

3. The method of claim 1 wherein the contacting is at a LHSV of 1 to 50.

4. The method of claim 1 wherein the hydrocarbon fraction contacts the alkali metal amide at 20° to 250° C.

5. The method of claim 1 wherein the amide is sodium amide.

6. The method of claim 5 wherein the fraction contains butadiene.

7. The method of claim 6 wherein the fraction contains isoprene.

* * * * *